Jan. 29, 1963 E. S. BOERNER Plant Pat. 2,223
ROSE PLANT
Filed April 2, 1962
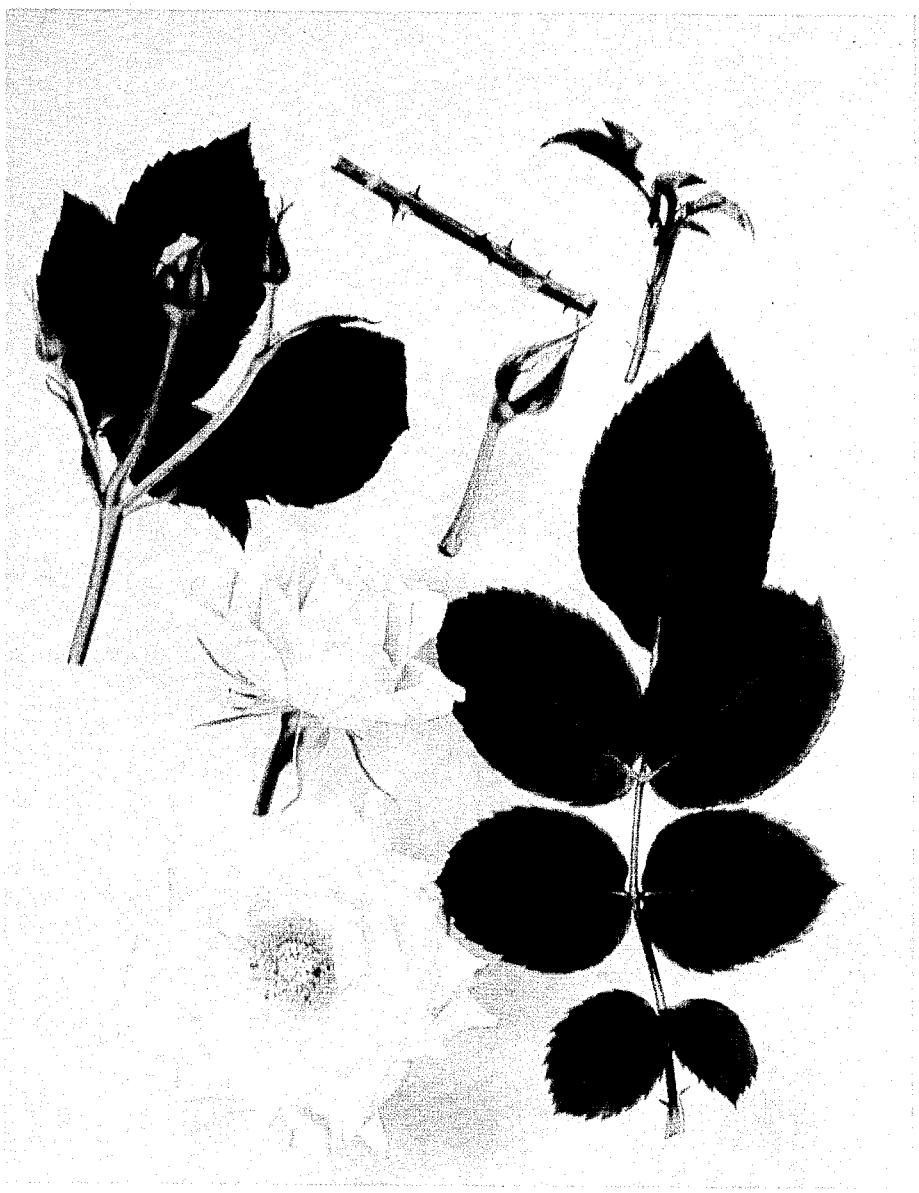
Inventor.
E. S. Boerner
By: Robb & Robb
Attorneys.

United States Patent Office

Plant Pat. 2,223
Patented Jan. 29, 1963

2,223
ROSE PLANT

Eugene S. Boerner, Newark, N.Y., assignor to Jackson & Perkins Company, Newark, N.Y., a corporation of New York Filed Apr. 2, 1962, Ser. No. 184,618
1 Claim. (Cl. 47—61)

The present invention relates to a new and distinct variety of rose plant of the floribunda class, which was originated by me by crossing the variety "Orange Mist" (Plant Patent No. 1,757) with the variety "Mayday" (Plant Patent No. 1,625).

The primary objective of this breeding was to produce a new rose variety of the floribunda type which bears crisp petaled flowers, combined with long-lasting flower qualities, with the flowers having an Apricot-Pink general color tonality. This objective was fully achieved, along with other desirable features as evidenced by the following unique combination of characteristics which are outstanding in the new variety and which distinguishes it from its parents, as well as from all other varieties of which I am aware:

(1) Crisp petaled flowers;

(2) A habit of holding the flower petals to the very end;

(3) Exceptionally long-lasting flower qualities as cut flowers, said flowers usually lasting from ten days to two weeks;

(4) A distinctive and attractive general color tonality of the flowers corresponding to Pale Yellow-Orange, very lightly overcast with Eosine Pink in the center and on the outer edges of the petals; and (5) A habit of good flower color retention, without appreciable loss of color after the flowers mature.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new veriety, with color terminology in accordance with Ridgway's Color Standards and Nomenclature:

Parentage: Seedling.
*Seed parent.*—"Orange Mist."
*Pollen parent.*—"Mayday."

Classification:
*Botanic.*—Floribunda.
*Commercial.*—Floribunda.

*Flower*

(Observations made from specimens grown in a greenhouse at Newark, New York, in the early afternoon during the latter part of the month of March.)

Blooming habit: Recurrent—continuous.

Bud:
*Size.*—Large.
*Form.*—Ovoid; is not affected by wet or hot weather.
*Color.*—When sepals first divide—Old Rose, Plate 13. When petals begin to unfurl—Light Jasper Red, Plate 13, with lower half of petals Picric Yellow, Plate 4. When half-blown: inside of petals—Grenadine Pink, Plate 2, lightly overcast with Pale Orange-Yellow, Plate 3; reverse of Petals—Pale Yellow-Orange, Plate 3, with outer edge of petals lightly overcast with Grenadine, Plate 2.
*Sepals.*—Slightly branched; curl back when petals begin to unfurl. Color: inside—Deep Lichen Green, Plate 33; outside—Deep Dull Yellow-Green, Plate 32.
*Calyx.*—Color—Chromium Green, Plate 32. Shape—funnel. Size—small. Aspect—smooth. Odor when rubbed—none.
*Peduncle.*—Length — medium. Aspect — rough. Color—Bice Green, Plate 17. Strength—erect; slender.
*Opening.*—Opens up well; is not affected by adverse weather conditions.

Bloom:
*Size.*—Large. Average size when fully expanded—from 3½ inches to 4 inches.
*Borne.*—Several together.
*Stems.*—Medium length; strong.
*Form (when first open).*—Cupped. Permanence—retains its form to the end.
*Petalage.*—Double (full but open center). Number of petals under normal conditions—30.
*Color.*—Center of flower—Pale Yellow-Orange, Plate 3, with center and outer edge of petals lightly overcast with Eosine Pink, Plate 1. Outer petals—Maize Yellow, Plate 4, with outer edge of petals lightly overcast with Safrano Pink, Plate 2. Base of petals (aiglet)—Light Cadmium, Plate 4. Inside of petals—Pale Yellow-Orange, Plate 3, very lightly overcast with Eosine Pink, Plate 1, in the center and on the outer edge of the petals. Reverse of petals—Shrimp Pink, Plate 1, with lower half of petals lightly overcast with Maize Yellow, Plate 4. General tonality from a distance—Pale Yellow-Orange, Plate 3, very lightly overcast with Eosine Pink, Plate 1.
*Discoloration.*—General tonality at end of first day—Pale Yellow-Orange, Plate 3, lightly overcast with Eosine Pink, Plate 1. Second day—Pale Yellow-Orange, Plate 3, very lightly overcast with Eosine Pink, Plate 1. Third day—Maize Yellow, Plate 4, lightly overcast with Safrano Pink, Plate 2.

Petals:
*Texture.*—Leathery; stiff; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—very long. As cut flower—very long; from 10 days to 2 weeks.

*Genital Organs*

Stamens, anthers: Medium size; many; arranged regularly around styles. Color—Light Orange Yellow, Plate 3.
Stamens, Filaments (threads): Medium length. Color—Light Cadmium Yellow, Plate 4.
Pollen: Color—Maize Yellow, Plate 4.
Styles: Bunched; uneven length; medium length; thin.
Stigmas: Color—Pale Green Yellow, Plate 5.
Ovaries: All enclosed in calyx.
Hips: None.
Seeds: None.

*Plant*

Form: Bush.
Growth: Vigorous; upright.
Foliage: Compound of 5–7 leaflets.
*Size.*—Large.
*Quantity.*—Abundant.
*Color.*—New foliage: upper side—Lettuce Green, Plate 5, with serrations Carmine, Plate 1; under side—Oil Green, Plate 5. Old foliage: upper side—Dark Cress Green, Plate 31, with serrations Carmine, Plate 1; under side—Bice Green, Plate 17.
*Shape.*—Oval pointed.
*Texture.*—Upper side—leathery. Under side—smooth.
*Ribs and veins.*—Ordinary.
*Edge.*—Serrated (saw-toothed).
*Serration.*—Both double and single; small.
*Leaf stem.*—Color—Calla Green, Plate 5. Under side—prickly.
*Stipules.*—Long; smooth.
Wood:
*New wood.*—Color—Oil Green, Plate 5. Bark—smooth.
Old wood.—Cress Green, Plate 31. Bark—smooth.

Thorns:
*Thorns.*—Quantity: on main stalks from base—many; on laterals from stalk—many. Form—narrow base; medium length; hooked downward. Color (when young)—Begonia Rose, Plate 1. Position—irregular.
*Prickles.*—Quantity: on main stalks—none; on laterals—none.
*Short needles.*—Quantity: on main stalks—none; on laterals—none.

I claim:

A new and distinct variety of rose plant of the floribunda class, substantially as herein shown and described, characterized particularly as to novelty by the unique combination of crisp petaled flowers, a habit of holding the flower petals to the very end, exceptionally long-lasting qualities of the flowers as cut flowers, a distinctive and attractive general color tonality of the flowers corresponding to Pale Yellow-Orange very lightly overcast with Eosine Pink in the center and on the outer edges of the petals, and a habit of retaining the flower color as the flowers mature.

No references cited.